(12) United States Patent
Wen

(10) Patent No.: US 7,067,089 B2
(45) Date of Patent: Jun. 27, 2006

(54) SANITIZING DEVICE AND METHOD FOR SANITIZING ARTICLES

(75) Inventor: Sheree H. Wen, 796 Longhill Rd. West, Briarcliff Manor, NY (US) 10510

(73) Assignee: Sheree H. Wen, Briarcliff Manor, NY (US)

(*) Notice: Subject to any disclaimer, the term of this patent is extended or adjusted under 35 U.S.C. 154(b) by 3 days.

(21) Appl. No.: 10/433,375

(22) PCT Filed: Nov. 7, 2002

(86) PCT No.: PCT/US02/35720

§ 371 (c)(1),
(2), (4) Date: Nov. 17, 2003

(87) PCT Pub. No.: WO03/039608

PCT Pub. Date: May 15, 2003

(65) Prior Publication Data

US 2005/0031485 A1    Feb. 10, 2005

Related U.S. Application Data

(60) Provisional application No. 60/337,654, filed on Nov. 7, 2001.

(51) Int. Cl.
*A61L 2/00* (2006.01)
(52) U.S. Cl. ............... 422/292; 422/28; 422/300
(58) Field of Classification Search ............... 422/121, 422/124, 21, 24, 186.3, 186.07, 292, 28, 422/32, 305, 300; 96/224, 227
See application file for complete search history.

(56) References Cited

U.S. PATENT DOCUMENTS

| 1,891,256 | A |   | 12/1932 | Bilde |
|-----------|---|---|---------|-------|
| 2,956,740 | A | * | 10/1960 | McGregor .................... 234/49 |
| 3,230,033 | A |   | 1/1966  | Hamilton et al. |
| 3,478,758 | A |   | 11/1969 | Davies |
| 3,817,703 | A |   | 6/1974  | Atwood |

(Continued)

FOREIGN PATENT DOCUMENTS

DE        3739979 A1    6/1989

(Continued)

*Primary Examiner*—Krisanne Jastrzab
*Assistant Examiner*—Sean E. Conley
(74) *Attorney, Agent, or Firm*—Robert D. Katz; Cooper & Dunham LLP

(57) ABSTRACT

The invention provides an apparatus for sanitizing a plurality of articles, which comprises a housing enclosing a sanitizing zone, the housing having a seal for preventing leakage of gas or fluid from the sanitizing zone; a pump for introducing an antimicrobial fluid into the sanitizing zone; and a pump for withdrawing the fluid from the sanitizing zone. The device also includes at least one high power microwave source and at least one ultraviolet irradiating source, or a microwave source that also generates ultraviolet radiation. Preferably, the gas is a halogen, such as chlorine, bromine, or iodine, or a gas or fluid containing chlorine or bromine ions, but it can be ozone or another gas which kills bacteria, microbes, viruses, and other pathogens. The fluid can also be sprayed droplets or vaporized sodium hypochlorite, or similar antiseptic agent.

9 Claims, 3 Drawing Sheets

U.S. PATENT DOCUMENTS

| | | |
|---|---|---|
| 3,915,180 A | 10/1975 | Jacobs |
| 3,926,556 A | 12/1975 | Boucher |
| 4,207,286 A | 6/1980 | Gut Boucher |
| 4,468,372 A | 8/1984 | Seifert et al. |
| 4,513,470 A | 4/1985 | Toya |
| 4,536,914 A | 8/1985 | Levine |
| 4,542,557 A | 9/1985 | Levine |
| 4,577,365 A | 3/1986 | Yuen |
| 4,591,485 A | 5/1986 | Olsen et al. |
| 4,610,048 A | 9/1986 | Ishihara et al. |
| 4,836,684 A | 6/1989 | Javorik et al. |
| 4,863,688 A * | 9/1989 | Schmidt et al. ............... 422/28 |
| 4,924,548 A | 5/1990 | Touya et al. |
| 5,114,670 A * | 5/1992 | Duffey ........................ 422/24 |
| 5,120,499 A | 6/1992 | Baron |
| 5,244,629 A | 9/1993 | Caputo et al. |
| 5,320,805 A | 6/1994 | Kramer et al. |
| 5,364,645 A | 11/1994 | Lagunas-Solar |
| 5,492,882 A | 2/1996 | Doughty et al. |
| 5,589,396 A | 12/1996 | Frye et al. |
| 5,593,476 A | 1/1997 | Coppom |
| 5,647,890 A | 7/1997 | Yamamoto |
| 5,651,811 A | 7/1997 | Frey et al. |
| 5,656,063 A | 8/1997 | Hsu |
| 5,725,623 A | 3/1998 | Bowerman et al. |
| 5,779,769 A | 7/1998 | Jiang |
| 5,927,304 A | 7/1999 | Wen |
| 5,944,873 A | 8/1999 | Jager et al. |
| 6,029,712 A | 2/2000 | Dougherty |
| 6,056,808 A | 5/2000 | Krause |
| 6,063,170 A | 5/2000 | Deibert |
| 6,094,775 A | 8/2000 | Behmer |
| 6,171,375 B1 | 1/2001 | Howie |
| 6,190,437 B1 | 2/2001 | Forsyth |
| 6,203,600 B1 | 3/2001 | Loreth |
| 6,295,692 B1 | 10/2001 | Shideler |
| 6,296,692 B1 | 10/2001 | Gutmann |
| 6,333,004 B1 | 12/2001 | Sheldon |
| 6,434,785 B1 | 8/2002 | Vandenbelt et al. |
| 6,468,433 B1 | 10/2002 | Tribelski |
| 2001/0043887 A1 | 11/2001 | Morneault |
| 2003/0085266 A1* | 5/2003 | Simon ........................ 232/27 |
| 2003/0145664 A1* | 8/2003 | Schwarz et al. ......... 73/863.22 |

FOREIGN PATENT DOCUMENTS

| | | |
|---|---|---|
| FR | 2599255 | 12/1987 |
| GB | 947699 | 9/1961 |
| GB | 2162424 | 2/1986 |
| JP | 62-282686 | 12/1987 |
| JP | 2-43984 | 2/1990 |
| JP | 405103610 A * | 4/1993 |
| JP | 405115540 A * | 5/1993 |

* cited by examiner

SANITIZING DEVICE AND METHOD FOR SANITIZING ARTICLES

This application claim the benefit of Provisional application Ser. No. 60/337,654, filed Nov. 7, 2001.

FIELD OF THE INVENTION

This invention relates to an apparatus for sanitizing articles such as envelopes, parcels, or packages sent by mail or courier, and more particularly to an apparatus which uses high energy microwave and ultraviolet radiation, along with a gas to kill contaminants such as bacteria and viruses on the surface or inside of the envelope or package.

BACKGROUND OF THE INVENTION

Machines resembling assembly lines through which food articles and the like pass use several different energy or radiation sources to sanitize the foodstuff, for example, to kill E. coli and botulism bacteria in the production plant. Cobalt 60, a radioactive material which emits gamma radiation, kills such bacteria, but the radioactive radiation it emits may expose plant workers to a hazard. Similarly, x-rays and electron beams can effectively kill undesirable organisms without rendering the foodstuff inedible, but they too present environmental hazards, and their cost of installation and power consumption may make them undesirable or impractical for either small scale or mass treatment of mail, packages, and the like.

It is therefore an object of the invention to provide a sanitizing apparatus which will effectively kill pathogens, such as bacteria, viruses, spores, mold, and the like on the surface and the interior of packages and envelopes.

SUMMARY OF THE INVENTION

The foregoing disadvantages of prior devices can be overcome by the present invention by providing an apparatus for sanitizing a plurality of articles, which comprises a housing enclosing a sanitizing zone, the housing having a seal for preventing leakage of gas or fluid from the sanitizing zone; a pump for introducing an antimicrobial fluid into the sanitizing zone; and a pump for withdrawing the fluid from the sanitizing zone. The device also includes at least one high power microwave source and at least one ultraviolet irradiating source, or a microwave source that also generates ultraviolet radiation. Preferably, the gas is a halogen, such as chlorine, bromine, or iodine, or a gas or fluid containing chlorine or bromine ions, but it can be ozone or another gas which kills bacteria, microbes, viruses, and other pathogens. The fluid can also be sprayed droplets or vaporized sodium hypochlorite, or similar antiseptic agent.

The invention also provides a method for killing microbes and pathogens on a plurality of articles, the method comprising: moving articles into a sanitizing zone; introducing an antimicrobial fluid in the presence of ultraviolet and microwave energy; and retaining the articles in the sanitizing zone for a period of time sufficient to kill microbial matter on the articles.

BRIEF DESCRIPTION OF THE DRAWINGS

Other objects, features and advantages of the invention may be understood by reviewing the following detailed description of the preferred embodiments in conjunction with the attached drawings in which.

DETAILED DESCRIPTION OF THE PREFERRED EMBODIMENTS

Figure 1:
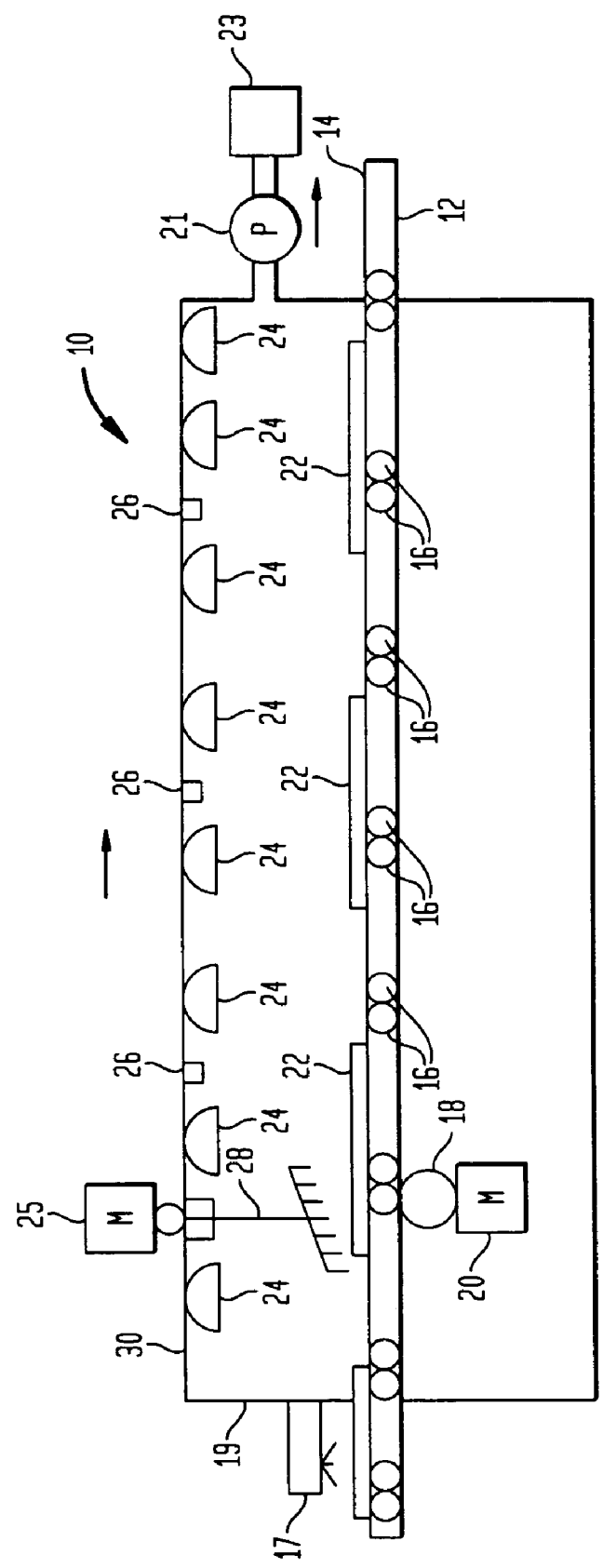
FIG. 1 is a schematic drawing of a first embodiment the sanitizing apparatus of the present invention.

Referring now to the drawings, a first embodiment of the present invention is shown in FIG. 1. The sanitizing device 10 includes conveyor belt 12 including a continuous belt 14 driven by rollers 16. Some of the rollers 16 are rotated by gears 18 driven by an electric motor 20. As in a conventional conveyor belt, the belt 14 carries along a plurality of articles 22 such as envelopes, packages, containers and the like. The sanitizing apparatus 10 of the present invention can therefore be used in a post office or other government facility, or in the mailroom of an office, bank, hotel, hospital, factory, or other business institution. Since it includes a conveyor 14, it can be installed as a module in a mail sorting or handling line.

The sanitizing assembly 10 of the present invention uses a plurality of ultraviolet and microwave radiation sources 24 to irradiate the sanitizing zone 19 through which packages or envelopes 22 pass through on the conveyor belt 14. Optionally, an x-ray detection system (not shown) can be used. The optional x-ray system can visualize the contents of the package or envelope to determine whether it contains any explosive or other hazardous device or substance. A metal sensing device 17 at the front of the conveyor such as a magnetometer or capacitance sensor recognizes packages with metallic packaging material, and an arm (not shown) shunts them aside to avoid exposure of metal to microwave radiation.

Additionally, the apparatus 10 includes a series of spigots 26 which introduce a fluid, such as a halogen gas (e.g., chlorine, iodine or bromine), ozone, a peroxide containing gas, chlorine dioxide gas, or a chlorine or chlorine and oxygen containing compound, such as calcium or sodium chloride or calcium or sodium hypochlorite. Other sources of chlorine ions or chlorine and oxygen containing ions may also be used, as may a carbohydrate containing substance or fluid, such as soy bean derivative. Fluid containing chlorine atoms, such as aqueous sodium hypochlorite (common household bleach) can be vaporized or sprayed into the chamber 19 as a mist of droplets. In such a case, the fluid will include chlorine and oxygen containing atoms, molecules or ions which will kill bacteria, viruses, or other microbial contaminants on the surface of the package 12.

Ultraviolet and microwave radiation would ionize or energize the gas or fluid so that it can react with and destroy biological material. The microwave and ultraviolet radiation by itself would not necessarily heat or irradiate the package sufficiently to kill bacteria or other contaminants, but would help the chlorine, ozone, peroxide or other gas to work more effectively.

Provision can be made to treat both sides of an envelope simultaneously, for example, by providing a mesh conveyor belt or a mechanism (not shown) to flip the envelopes over to complete treatment of a second side. In either case, the article 22 is held for a time sufficient to allow the energized ions, atoms, or molecules to kill the microbes on the surface of the article. U.S. Pat. Nos. 3,817,703 and 5,364,645 both address using various forms of electromagnetic radiation to kill pathogens and microorganisms, and set forth suggested time and energy levels which may be effective in the present apparatus and method. The contents of those patents are incorporated by reference herein.

Figure 3:
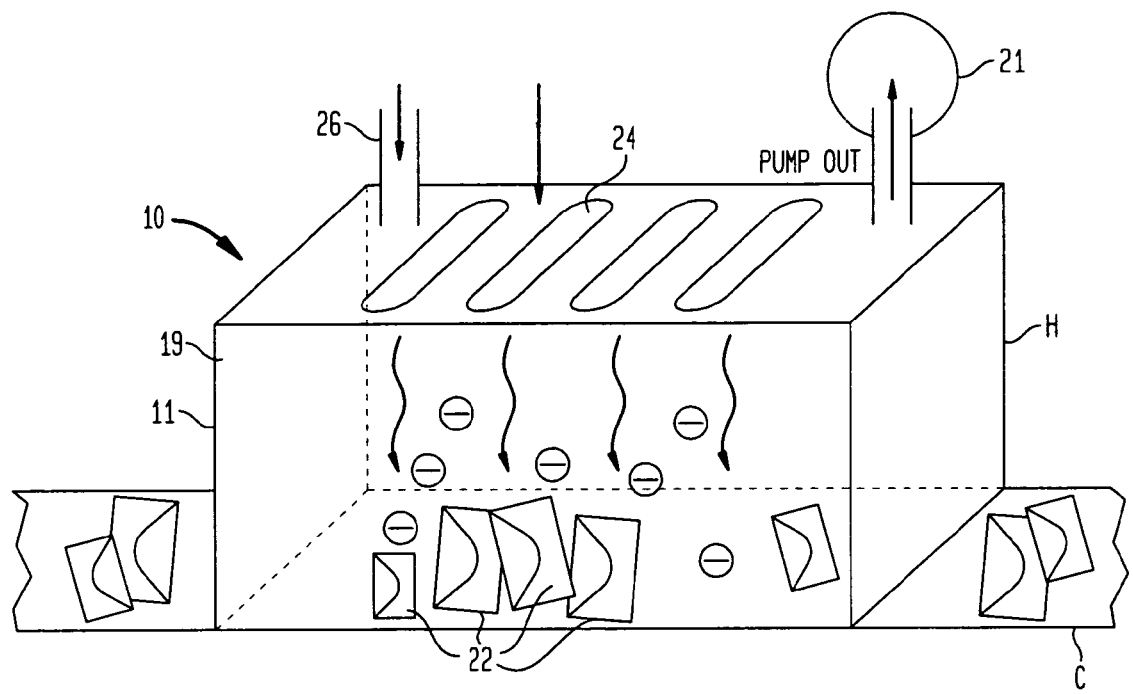
FIG. 3 is a schematic drawing of a second embodiment of the present invention.

In a second embodiment, shown schematically in FIG. 3, the article sanitizer 10 can be in the form of a module 11 to add to an existing conveyor belt C used in a postal or sorting facility. Like the previous embodiment, module 11 could include one or more means for introducing an antimicrobial fluid into a sanitizing zone 19 defined by the housing H. The module 11 also includes one or more ultraviolet and microwave radiation sources which may be separate or included in a single unit, as shown in FIG. 3. The second embodiment, like the first, includes a pump 21 for removing antimicrobial fluid from the sanitizing zone or chamber 19. The chamber 19, in any embodiment, should preferably include a series of baffles and gaskets to prevent the antimicrobial gas or other fluid, as well as the radiation, from escaping from the chamber 19.

Figure 4:
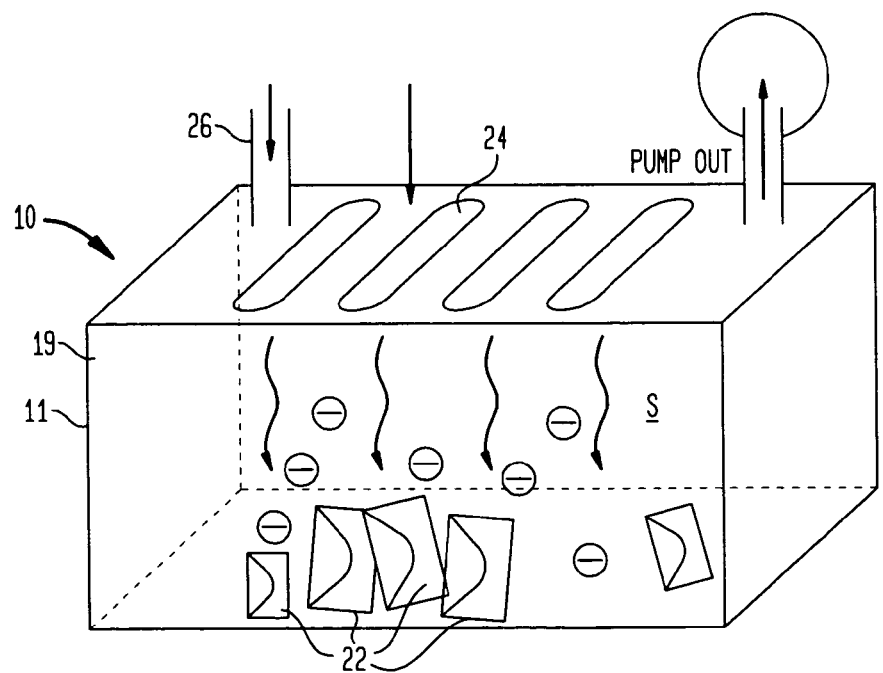
FIG. 4 is a schematic drawing of a third embodiment of the present invention.

In yet another embodiment, illustrated in FIG. 4, the sanitizing apparatus 10 of the present invention may be a module 11 which, in lieu of a conveyor 19, a housing 19 which rests on a table or similar support (not shown). The housing 19 contains the articles 22 which undergo sanitation in an enclosed space S. The space S has walls which allow an operator to insert articles 22, and then close the housing 19 to prevent leakage of antimicrobial fluid and radiation from the housing 19. The apparatus 10 also includes a pump 26 for introducing the fluid into the chamber or space and a pump 21 for removing the fluid and filtering solid matter there from.

The present invention can also advantageously employ a perforating mechanism 28 to make tiny holes in the envelope or other package to allow the gas to penetrate the interior of the parcel 22, killing any pathogens contained therein. In the embodiment shown in FIG. 1, the microperforating apparatus 28 is a series of pins mounted on an arm which raises and lowers through a reciprocal motion driven by a motor-cam combination 25. The arm raises and lowers as directed by an electric eye or other detector, which would lift the arm sufficiently to allow a package to pass underneath. It can be lowered so that the tines on the arm perforate the package wrapper slightly without harming the contents. The pinpricks in the package would allow the chlorine or other fluid to enter the interior of the package in order to destroy anthrax or other biohazard, for example, or to allow the spores or microbes to exit the package where they will be destroyed by the antimicrobial fluid. Alternatively, a series of rollers studded with pins or teeth can be used to provide the perforations (not shown). The rollers should move up and down to adjust for different package sizes, but should have a spring or other opposing force mechanism pressing them downward toward the package 22 so that they lightly perforate the cover layers of the package.

A laser 54, such as an excimer laser (see FIG. 2) can provide also light energy to kill microbes and other pathogens. Examples of methods using laser and ultraviolet radiation to disinfect foods may be found in U.S. Pat. No. 5,364,645 (Lagunas-Solar), and U.S. Pat. No. 3,817,703 (Atwood), referenced above. Optionally, an x-ray or other radioactive source can be added, to be used in combination with the high power microwave and UV energy sources incorporated into the present invention.

Figure 2:
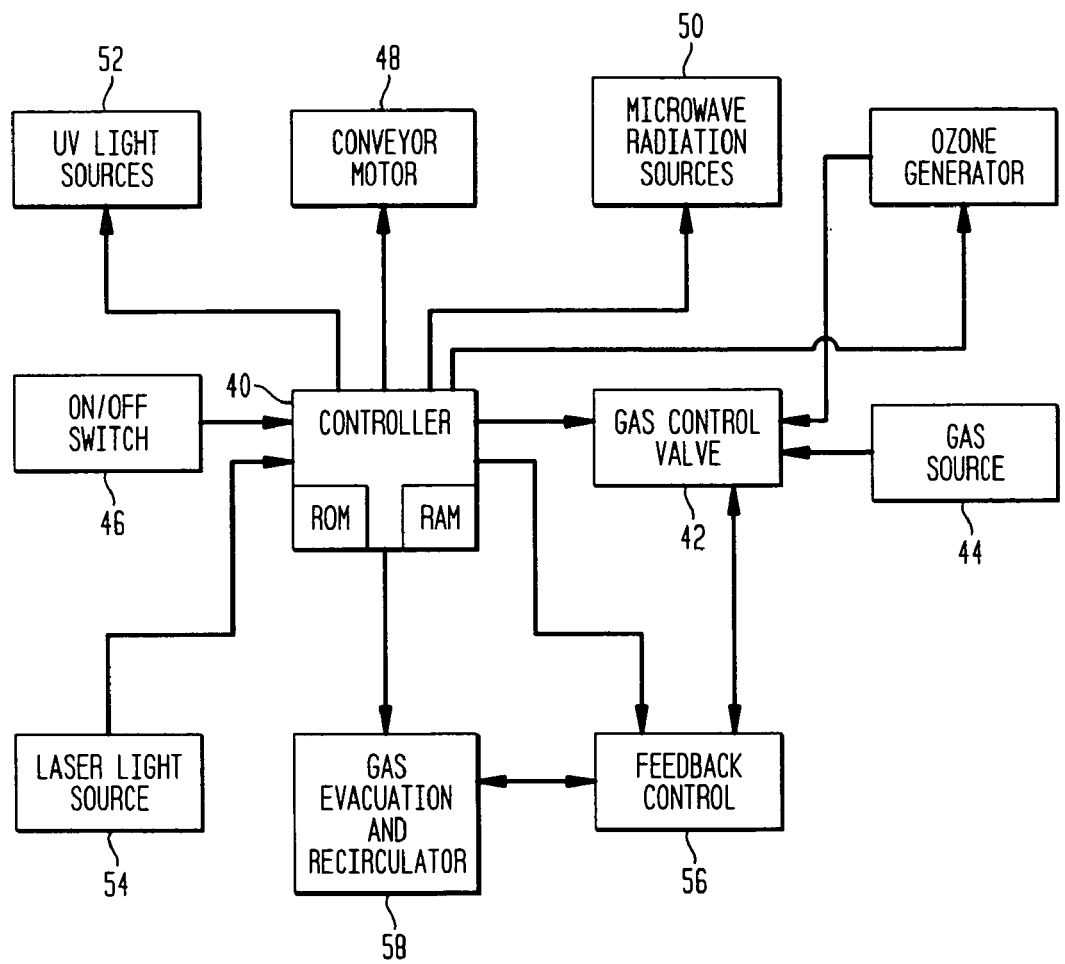
FIG. 2 is a block diagram of circuitry for controlling a sanitizing apparatus according to an embodiment of the present invention.

The apparatus 10 also includes a feedback control system 56, whose operation may be understood with reference to FIG. 2. The 56 system includes a controller 40 to control the amount of energy and gasses released during the operation of the system. Controller 40 includes preprogrammed ROM to control the motor 20 which drives the conveyor belt 14, either incrementally, or linearly.

Controller 40 also controls one or more solenoid or similar type gas or fluid valves 42 through a feedback loop so that the proper disinfecting concentration of gas (for example, ozone, peroxide, chloride, or chlorine) is fed from the gas source 44 into the treatment chamber 19 (FIG. 1) of the apparatus 10. The system 10 is activated by an on/off switch 46 which activates the motor 48 driving the conveyor 14. The controller 40 also switches and controls the microwave radiation source 50, the ultraviolet light source 52, and the optional laser light source 54. The controller 40 either includes, or works in tandem with a feedback control system 56 to regulate the flow of gas, and the intensity of light or energy in the treatment chamber 19. The system 10 preferably includes a gas evacuation and recirculation system 58 including a filter for particulate matter, so that gas used in the treatment apparatus 10 can be reclaimed and recycled or reused.

Controller 40 can also be any suitable type of controller circuit and, for example, can consist of a microprocessor controller. Various types of controllers suitable for use in a device such as the present invention are known in the art. Accordingly, controller 40 will not be described in detail. Briefly, however, controller 40 includes ROM for storing one or more operating programs. Controller 40 can also include RAM that can be programmed by the user through use of an alphanumeric control pad (not shown). Of course, controller 40 can also include various other types of memories and/or peripherals or peripheral interfaces as desired. Controller 40 can also be preprogrammed or can be programmed by the user to automatically run in cycles.

The UV light source may be a monochromatic beam of pulsed ultraviolet or ultraviolet laser radiation having a wavelength of about 240–280 nm. Any type of ultraviolet source producing enough energy to kill pathogens, including Hg lamps emitting 20 nm UV radiation, or low intensity (0.10–10 W/m$^2$) continuous wave polychromatic (broad band) UV radiation can be used. Also desirable would be low intensity (0.10 to 10 W/m$^2$) continuous wave polychromatic (broad band) UV radiation (4.88 eV). Pulsed (20 nsec) ultraviolet laser radiation of 193 nm (6.42 eV) may also be used under certain conditions.

In operation, with reference to FIGS. 1 and 2, the conveyor belt 14 moves when the on/off switch 46 is turned "on". The high intensity UV light source 52 and microwave radiation source 50 irradiate the parcels, packages or envelopes 22 on the conveyor belt 14. The controller 40 opens the solenoid or other control on the gas or fluid control valve 42, allowing gas or fluid to enter from its source or container, such as a gas tank 44, to enter the chamber 19. The high intensity UV and microwave radiation ionizes the gas inside the chamber 19, which in turn kills microbes, such as anthrax or other harmful bacteria or viruses. The contaminated gas is removed by the pump 21, which connects to a filter 23 to remove harmful bacteria and other particulate matter. It may also cleanse the gas so that some or all may be reused.

Various modifications in the construction of the present apparatus 10 may be made to adapt to a particular type of package, or to use it, for example, to decontaminate food. While several embodiments have been shown and described, it will be apparent that other adaptations and modifications can be made without departing from the spirit and scope of the invention.

I claim:

1. An apparatus for sanitizing a plurality of envelopes, parcels, or packages sent by mail or courier, comprising:
a housing enclosing a sanitizing zone, the housing having a seal for preventing leakage of gas from the sanitizing zone; a source of antimicrobial fluid: a pump for introducing an antimicrobial fluid into the sanitizing zone; means for making a plurality of holes in an envelope, parcel or package to allow the antimicrobial fluid to penetrate the interior of the envelope, parcel or package; a pump for withdrawing the antimicrobial fluid from the sanitizing zone; and at least one microwave source and at least one ultraviolet irradiating source.

2. An apparatus in accordance with claim 1, wherein the pump for withdrawing the antimicrobial fluid includes a filter for removing particulate matter from the fluid.

3. An apparatus in accordance with claim 1, wherein the antimicrobial fluid is ozone, a peroxide, a halogen gas, or chlorine dioxide.

4. An apparatus in accordance with claim 1, wherein the microwave and ultraviolet sources emit microwave and ultraviolet energy to ionize the antimicrobial fluid in the sanitizing zone.

5. An apparatus in accordance with claim 4, wherein the housing mounts adjacent a conveyor apparatus such that the conveyor carries the articles through the sanitizing zone.

6. An apparatus in accordance with claim 4, wherein the housing additionally comprises a conveyor for moving envelopes, parcels, and packages through the sanitizing zone.

7. A method for destroying microbes on a plurality of envelopes, parcels, or packages sent by mail or courier, the method comprising: moving the plurality of envelopes, parcels or packages into a sanitizing zone; making a plurality of holes in the envelopes, parcels or packages to allow antimicrobial fluid to penetrate the interior thereof; introducing the antimicrobial fluid in the presence of ultraviolet and microwave energy; and retaining the envelopes, parcels or packages in the sanitizing zone for a period of time sufficient to kill microbial matter on and in the interior of the envelopes, parcels or packages.

8. A method according to claim 7, wherein the holes are pinpricks.

9. A method according to claim 7, wherein the ultraviolet and microwave energy ionize the antimicrobial fluid when the envelopes, parcels, and packages are in the sanitizing zone.

* * * * *